US008820319B2

(12) United States Patent
Schwartz et al.

(10) Patent No.: US 8,820,319 B2
(45) Date of Patent: Sep. 2, 2014

(54) GUIDE DEVICE FOR TRACHEAL INTUBATION

(75) Inventors: John Schwartz, Williamston, MI (US); Richard Schwartz, Evans, GA (US)

(73) Assignee: AI Medical Devices, Inc., Williamston, MI (US)

( * ) Notice: Subject to any disclaimer, the term of this patent is extended or adjusted under 35 U.S.C. 154(b) by 1369 days.

(21) Appl. No.: 11/906,870

(22) Filed: Oct. 4, 2007

(65) Prior Publication Data

US 2009/0090357 A1   Apr. 9, 2009

(51) Int. Cl.
*A61M 16/00* (2006.01)
*A62B 9/06* (2006.01)

(52) U.S. Cl.
USPC .............................. 128/200.26; 128/207.14

(58) Field of Classification Search
CPC ............ A61M 16/0488; A61M 16/04; A61M 16/0402; A61M 16/0431; A61M 16/0463; A61M 16/04976; A61M 16/049; A61M 16/0495
USPC .............. 128/200.26, 200.24, 207.14, 204.18
See application file for complete search history.

(56) References Cited

U.S. PATENT DOCUMENTS

| | | | |
|---|---|---|---|
| 2,756,742 A | 7/1956 | Barton | |
| 4,054,135 A | 10/1977 | Berman | |
| 4,067,331 A | 1/1978 | Berman | |
| 4,068,658 A | 1/1978 | Berman | |
| 4,069,820 A | 1/1978 | Berman | |
| 4,306,547 A * | 12/1981 | Lowell | 600/188 |
| 4,454,887 A * | 6/1984 | Kruger | 600/585 |
| 4,612,927 A | 9/1986 | Kruger | |
| 4,832,020 A | 5/1989 | Augustine | |
| 5,024,218 A * | 6/1991 | Ovassapian et al. | 128/200.26 |
| 5,053,166 A | 10/1991 | Murase et al. | |
| 5,174,283 A | 12/1992 | Parker | |
| 5,203,320 A | 4/1993 | Augustine | |
| 5,323,771 A | 6/1994 | Fisher et al. | |
| 5,339,805 A * | 8/1994 | Parker | 128/200.26 |
| 5,720,275 A | 2/1998 | Patil et al. | |
| 5,743,254 A * | 4/1998 | Parker | 128/200.26 |
| 5,845,634 A * | 12/1998 | Parker | 128/200.26 |
| 6,053,166 A | 4/2000 | Gomez | |
| 6,474,332 B2 * | 11/2002 | Arndt | 128/200.26 |
| 6,539,942 B2 | 4/2003 | Schwartz et al. | |
| 6,568,388 B2 * | 5/2003 | Christopher | 128/200.26 |
| 2002/0117171 A1 * | 8/2002 | Parker | 128/200.26 |
| 2006/0272647 A1 * | 12/2006 | Hauge | 128/207.16 |

FOREIGN PATENT DOCUMENTS

WO        WO98/41137 A1        9/1998

OTHER PUBLICATIONS

International Preliminary Report on Patentability and Written Opinion of the International Searching Authority dated Dec. 16, 2008, for Application No. PCT/US08/011280.

* cited by examiner

*Primary Examiner* — Rachel Young
(74) *Attorney, Agent, or Firm* — Butzel Long (57) ABSTRACT

A guide adapted for facilitating insertion of a medical device into the trachea of a patient is disclosed. The guide includes an integral curved-shaped member having at least a first leg at one end of the guide. The curved-shaped member essentially includes an outside curved side defining a concave groove. A first angle is defined on the first leg configured and dimensioned to allow for at least the first leg to pass through the mouth and into the trachea of the patient. Insertion of the guide into the trachea allows for elevation of the tongue and surrounding soft tissue of the patient thereby forming an air space that allows for passage of a medical device.

14 Claims, 5 Drawing Sheets

FIG. 1

GUIDE DEVICE FOR TRACHEAL INTUBATION

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION (1) Field of the Invention

The present invention relates generally to a guide device related to endrotracheal intubation, and more specifically to a guide device having a curvable portion.

(2) Description of the Related Art

U.S. Pat. Nos. 4,054,135, 4,067,331, 4,068,658, and 4,069,820 to Berman teach an intubating pharyngeal airway having a side access for passage of a tube on the said airway comprising a flanged stop at the proximal end, a curved airway central tubular member and a distal ball tip adapted to fit into the vallecular. The side opening may be expanded or closed by means of either a hinge on the opposite side wall of the tube or by a cap or insert closure.

U.S. Pat. No. 4,612,927 issued to Kruger relates to an instrument for keeping clear the upper respiratory passages and for performing intubations, in which a tube which is to be inserted may have its distal extremity moved as far as into the windpipe via a passage acting as a guide. The passage is constructed as a channel extending within the instrument shaft, whereas the distal instrument extremity comprises a head before which terminates the channel and which is intended to be placed in contact against the larynx upon inserting the instrument. The instrument head acting as a stop will thus limit the maximum depth of insertion.

U.S. Pat. No. 5,203,320 issued to Augustine discloses a tracheal intubation guide having a tubular member with a curved forward end shaped to follow the curvature of the back of the tongue and throat of a patient, and a rear end for projecting out through the mouth of the patient, and an anterior guide surface extending along at least part of the length of the member to its forward end for guiding the member into the throat into a position opposite the opening into the larynx. The tubular member has a through bore for holding an endotracheal tube, and the guide surface has a forward edge of concave shape for engaging the front of the epiglottis and seating over the hyo-epiglottic ligament when the member is accurately positioned. Correct positioning can be detected by external palpation of the neck.

U.S. Pat. No. 5,053,166 issued to Gomez discloses an intubating assembly used to position an intubation tube having a distal end, a proximal end and a generally resilient tubular configuration, into a trachea of a patient. The intubating assembly is described as having a guide assembly that receives the intubation tube therein and conforms the intubation tube to its configuration. The guide assembly includes first and second introduction segments hingedly coupled to one another and positionable between a closed orientation, which defines a generally curved configuration of the guide assembly, and an open orientation, which defines a generally straight configuration of the guide assembly. The intubating assembly further includes a positioning assembly structured to selectively position the first and second introduction segments between the open orientation. The intubation tube is generally straightened to facilitate direct introduction thereof into an airway of the patient to a point posterior of a tip of an epiglottis of the patient and the closed orientation. The intubation tube is generally curved in order to angle the distal end thereof towards the trachea of the patient and thereby introduce the intubation tube directly into the trachea of the patient.

U.S. Pat. No. 6,539,942 issued to Schwartz et al., hereby incorporated herein by reference in its entirety, describes an endotracheal intubation device having a series of interlinked, truncated ring-like elements disposed along the distal portion of the tube and a handgrip for controlling the degree of bend in the distal end of the device. An imaging device, such as a nasopharyngoscope, can be inserted through the intubation device to visualize the patient's vocal cords during the intubation procedure. The endotracheal intubation device uses a scissors mechanism without pulleys to bend the distal end of the device.

While the related art teach endotracheal intubation devices, there still exists a need for an improved endotracheal device having a curvable portion so as to facilitate the insertion of an endotracheal tube into a patient.

OBJECTS

Therefore, it is an object of the present invention to provide an improved guide for an endotracheal intubation device having a curvable portion.

These and other objects will become increasingly apparent by reference to the following description.

SUMMARY OF THE INVENTION

The present disclosure relates to a guide adapted for facilitating insertion of a medical device into the trachea of a patient, which comprises: (a) opposed ends; and (b) an integral curve-shaped member having at least a first leg at one end of the guide. The curved-shaped member consists essentially of: (i) opposed facing sides; (ii) an inside curved side formed between the facing sides; and (iii) an outside curved side positioned opposite the inside curved side formed between the facing sides. The inside curved side of the at least a first leg defines a first angle configured and dimensioned to allow for at least the first leg to pass through the mouth and into the trachea of the patient. The outside curved side defines a concave groove extending along the at least a first leg. Insertion of the guide into the trachea allows for elevation of the tongue and surrounding soft tissue of the patient thereby forming an air space that allows for passage of a medical device.

In an exemplary embodiment, the guide associated with the present disclosure further comprises a maneuvering member positioned at the opposite end of the guide with respect to the at least a first leg adapted to allow for manual control over the position of the first leg relative to the trachea. The maneuvering member can be a handle.

In a further exemplary embodiment, a guide associated with the present disclosure comprises an integral curve shaped member that defines a U-shape geometry further comprising an opposed second leg at the opposite end of the guide relative to the first leg. The end of the guide including the at least a first leg can be rounded. In a further embodiment, each of the opposed ends of the guide can be rounded to enable insertion of guide into the trachea.

The first angle associated with an exemplary guide typically defines an angle A1 of about 50 to 85°. A guide can comprise a second leg that defines a second angle configured and dimensioned to allow for the second leg to pass through the mouth and into the trachea of the patient. Generally, the first angle defines an angle A1 of about 50 to 85° and the second angle defines an angle A2 of about 20 to 60°. In an exemplary embodiment, the first leg defines an angle A1 which is about 80° and the second leg defines an angle A2 which is 45°. Typically, the inside curved side defines a curved length of about 7 to 12 inches. Each of the opposed facing sides can define a uniform outer thickness extending from each end of the guide. The uniform thickness can measure from about 0.5 inches to 2 inches.

An exemplary guide associated with the present disclosure defines a concave groove that is configured and dimensioned to define the air space after insertion of the guide into the trachea. The medical device can comprise an endoscope adapted to be received along a surface of the concave groove. The medical device can further comprise an airway. In an exemplary embodiment, the concave groove is configured and dimensioned to define an airspace that allows for insertion of the medical device to reach a target region of the patient and passing by the vocal cords. The airspace defined by the concave groove allows for insertion of the medical device such that the medical device avoids direct physical contact with the vocal cords.

Typically, the concave groove forms a curvature extending from each of the opposed facing sides and defining a smooth surface adapted to allow for the medical device to follow the guide to reach a target tissue region and avoiding contact with the vocal cords and surrounding soft tissue associated with the patient. An exemplary guide can comprise at least a first leg that is fabricated from a material selected from the group consisting of polycarbonate, nylon, and metal.

The present disclosure further provides for a method for facilitating insertion of a medical device into the trachea of a patient comprising the steps of: (a) inserting a guide into the trachea of the patient, the guide comprises: (1) opposed ends; (2) an integral curve-shaped member having at least a first leg at one end of the guide, the curved-shaped member consisting essentially of: (i) opposed facing sides; (ii) an inside curved side formed between the facing sides; and (iii) an outside curved side positioned opposite the inside curved side formed between the facing sides; wherein the inside curved side of the at least a first leg defines a first angle configured and dimensioned to allow for at least the first leg to pass through the mouth and into the trachea of the patient; wherein a concave groove is formed along the outside curved side extending along the at least a first leg; and wherein insertion of the guide into the trachea allows for elevation of the tongue and surrounding soft tissue of the patient to form an air space passageway that allows for passage of a medical device; (b) forming a passageway for the medical device to reach a target region by elevating the tongue and surrounding soft tissue of the patient with the inserted guide; and (c) inserting the medical device into the trachea to reach the target tissue region such that the medical device follows along a pathway defined by the concave groove formed on the outside curved side of the guide.

An exemplary method can further comprise a maneuvering member positioned at the opposite end of the guide with respect to the at least a first leg adapted to allow for manual control over the position of the first leg relative to the patients trachea. The maneuvering member can be a handle. In an exemplary embodiment, the integral curve shaped member defines a U-shape geometry further comprising an opposed second leg at the opposite end of the guide relative to the first leg. Typically the end of the guide including the at least a first leg is rounded. In an exemplary embodiment, each of the opposed ends of the guide are rounded to enable insertion of guide into the trachea.

The first angle associated with a guide of an exemplary method typically defines an angle A1 of about 50 to 85°. A guide can comprise a second leg that defines a second angle configured and dimensioned to allow for the second leg to pass through the mouth and into the trachea of the patient. Generally, the first angle defines an angle A1 of about 50 to 85° and the second angle defines an angle A2 of about 20 to 60°. In an exemplary embodiment, the first leg defines an angle A1 which is about 80° and the second leg defines an angle A2 which is about 45°. Typically, the inside curved side defines a curved length of about 7 to 12 inches. Each of the opposed facing sides can define a uniform outer thickness extending from each end of the guide. The uniform thickness can measure from about 0.5 inches to 2 inches.

An exemplary guide associated with an exemplary method associated with the present disclosure defines a concave groove that is configured and dimensioned to define the passageway after insertion of the guide into the trachea. The medical device can comprise an endoscope adapted to be received along a surface of the concave groove. The medical device can further comprise an airway. In an exemplary embodiment, the concave groove is configured and dimensioned to define a passageway that allows for insertion of the medical device to reach a target region of the patient and passing by the vocal cords. The passageway defined by the concave groove allows for insertion of the medical device such that the medical device avoids direct physical contact with the vocal cords.

Typically, the concave groove forms a curvature extending from each of the opposed facing sides and defining a smooth surface adapted to allow for the medical device to follow the guide to reach a target tissue region and avoiding contact with the vocal cords and surrounding soft tissue associated with the patient. An exemplary guide associated with an exemplary method can comprise at least a first leg that is fabricated from a material selected from the group consisting of polycarbonate, nylon, and metal.

The present disclosure further provides for an exemplary method wherein the medical device is an endoscope and the method further comprises the steps of: (i) inserting the endoscope into the trachea along the passageway formed by the guide; (ii) positioning the guide in a desired position and orientation using the image generated through the endoscope; and (iii) inserting an airway to reach a target tissue region following along the guide to avoid causing harm to the surrounding soft tissue, the vocal cords, and the esophagus.

DETAILED DESCRIPTION OF THE INVENTION

All patents, patent applications, government publications, government regulations, and literature references cited in this specification are hereby incorporated herein by reference in their entirety. In case of conflict, the present disclosure, including definitions, will control.

The term "curvable portion" as used herein refers to a part of the tubular element associated with an exemplary endoscope apparatus which is curvable. In some embodiments, the curvable portion is provided as a portion with cuts (as slits, wedges etc.) as in the two alternate embodiments described in U.S. patent application Ser. No. 11/514,486 to Schwartz et al. hereby incorporated herein by reference in its entirety. In other embodiments, the curvable portion comprises a series of vertebra as described in U.S. Pat. No. 6,539,942 and U.S. patent application Ser. No. 11/230,392 to Schwartz et al., each of which are hereby incorporated herein by reference in their entirety. The curvable portion can also be provided as a bellows or other tubular structures that can be curved which are known in the art.

The term "tubular element" as used herein refers to an elongate member, including but not limited to a tubular element described herein. The tubular element can be cylindrical; however it is not limited thereto. Any elongate shape that an endotracheal tube can slide over is encompassed by the present invention.

The term "imaging system" as used herein refers to any mechanism or device for collecting an image of the throat of the patient at the distal end of the tubular element during the endotracheal intubation procedure. An example of a viewing means includes, but is not limited to, a small video camera or a lens for a fiber optics system.

The term "imaging system" as used herein further refers to any mechanism or device for visualizing or displaying an image of the throat of the patient at the distal end of the tubular element during the endotracheal intubation procedure. An example of a visualizing means includes, but is not limited to, a liquid crystal display or other type of video display. Other examples included one or more lenses which collect an image from a fiber optics system to be viewed in an eyepiece.

U.S. patent application Ser. Nos. 11/880,117, 11/230,392 and 11/514,486 to Schwartz et al., hereby incorporated herein by reference in their entirety, describe endotracheal intubation devices. In an exemplary embodiment, the present disclosure provides for a guide effective to operate in cooperation with these devices. More particularly, a guide according to the present invention facilitates effective endotracheal device insertion into a patient's throat and trachea to reach a target tissue region. The present disclosure provides for a guide device to facilitate endotracheal intubation of a patient.

According to Ser. No. 11/880,117, a particular exemplary endotracheal device comprises: a support means; a tubular element that is cantilevered at a proximal end from the support means, having an opposed distal end for insertion into the patient's mouth to place an endotracheal tube. The device further comprises a curvable portion of the tubular element disposed adjacent to the distal end of the tubular element. A gripping means that is attached to the support means is disposed forward of the proximal end of the tubular element, such that a length of the tubular element projects over the gripping means. A control means is provided as a component of or adjacent to the gripping means as well as a means for moving the curvable portion transmitting a force applied by the user on the control means to curve the curvable portion. When the control portion is manipulated by the user the curvable portion curves into a generally curved configuration in a controlled manner from a fully straight or less curved configuration and returns to the less curved conformation when the control means is released.

Other medical devices used for intubation and various medical procedures can be inserted into a patients throat. To avoid physical interaction or contact with soft tissue regions such as the vocal cords, precise or guided insertion is desirable.

Figure 1:
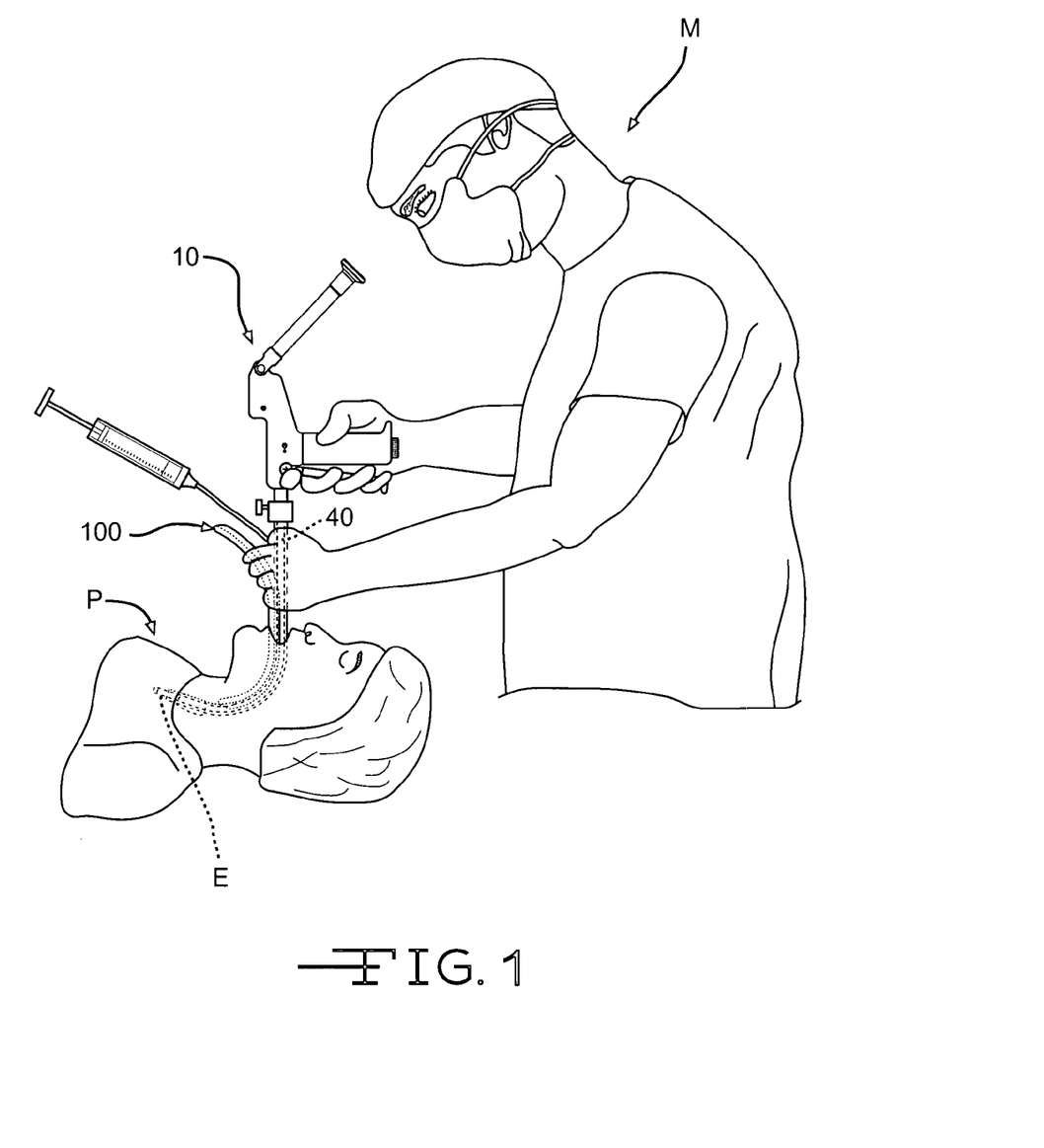
FIG. 1 illustrates an environmental perspective view of one embodiment of an endotracheal intubation device in use in cooperation with an exemplary guide associated with the present disclosure.

Referring to FIGS. 1-6, an exemplary guide 100 is illustrated over several views and while in use in facilitating intubation of patient P. As illustrated in FIG. 1, an exemplary intubation device 10 as described in Ser. No. 11/880,117 is being inserted into the mouth of patient P. Intubation device 10 comprises a tubular element 40 that comprises an endoscope E. Upon insertion into the throat of patient P, tubular element 40 follows a pathway defined by a smooth surface 101 of concave groove 102 of exemplary guide 100 as seen with respect to FIGS. 2 and 3. In a particular embodiment, guide 100 is first inserted into the trachea of patient P thereby allowing for a medical professional M to elevate the tongue and soft tissue of patient P. This elevation of the tongue and soft tissue defines a air space (also referred to as a passageway). The passageway allows for insertion of tubular element 40 of intubation device 10 relatively easily following along guide 10 as shown with respect to FIG. 1. Typically, this allows for insertion of tubular element 40 quickly and safely without causing damage to a patient's sensitive soft tissues such as the vocal cords.

Figures 2, 3:
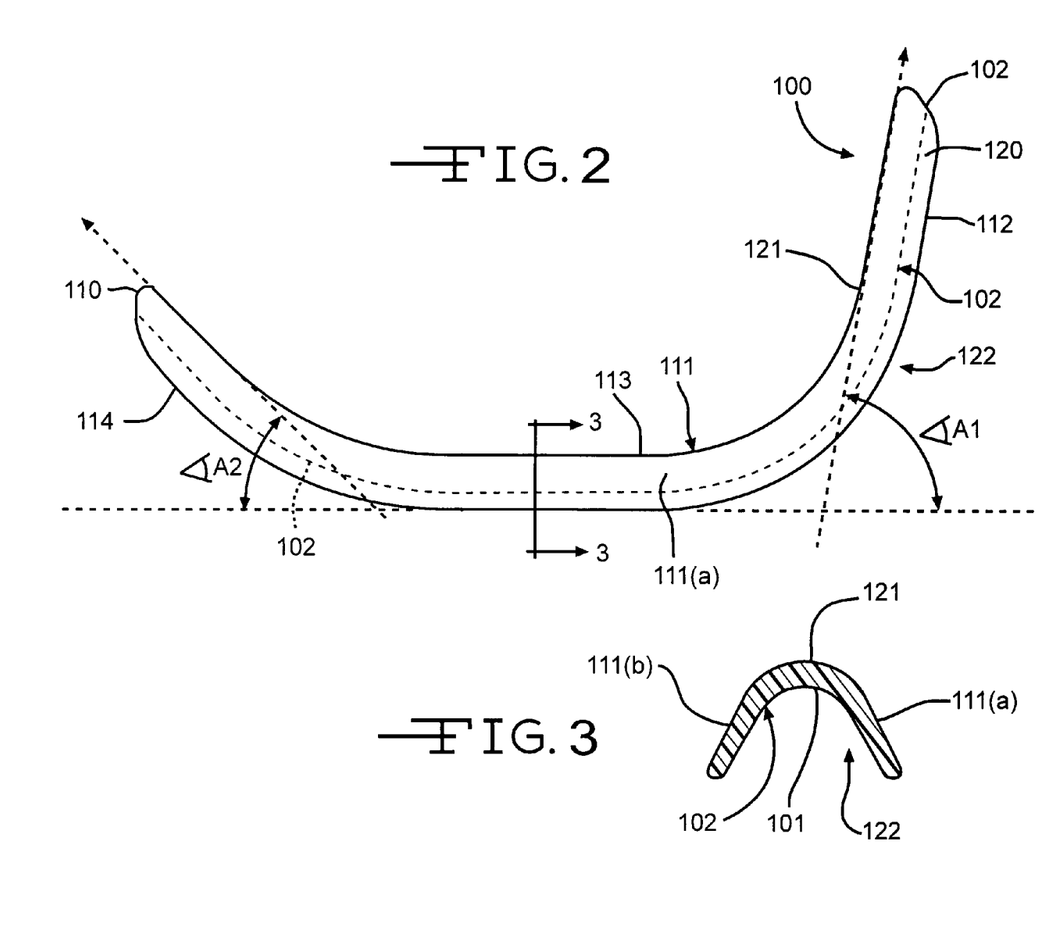
FIG. 2 illustrates a side cross-sectional view of an exemplary guide associated with the present disclosure.
FIG. 3 illustrates an axial cross sectional view of the guide illustrated in FIG. 2 taken along line 3-3 of FIG. 2.

FIGS. 2 and 3 illustrate a side view and a cross sectional view of an exemplary guide 100 respectively. Typically, guide 100 comprises opposed ends 110 and 120 and an integral curved-shaped member 111 having at least a first leg 112 at end 120. Curved-shape member 111 further comprises opposed facing sides 111(a) and 111(b). Inside curved side 121 is formed between opposed facing sides 111(a) and 111(b), typically along the inner curvature associated with guide 100. Outside curved side 122 is formed between opposed facing sides 111(a) and 111(b) opposite of inside curved side 121.

The inside curved side 121 typically defines a first angle A1. Angle A1 is generally defined at the curving portion in which first leg 112 curves into center portion 113 of member 111. Angle A1 can be an angle from about 20-85 degrees. In an exemplary embodiment, angle A1 is about 80 degrees. Exemplary angles can be measured from center portion 113 angled towards end 120. Angle A1, also referred to as a first angle, is configured and dimensioned to allow for at least the first leg 112 to pass through the mouth and into the trachea of the patient. Angle A1 can be further configured and dimensioned to define a passageway for an exemplary medical device to effectively avoid harming or contacting surrounding soft tissue regions such as the vocal cords during insertion to reach a target tissue region.

Still with reference to FIGS. 2 and 3, outside curved side 122 defines a concave groove 102 extending along at least the length of first leg 112. Typically groove 102 extends along center portion 113 uniformly. Groove 102 typically defines a parabolic geometry thereby forming a relatively smooth surface 101. The parabolic cross section of the concave groove 102 is open to the surrounding environment. Thus, a medical device following along smooth surface 101 is not enclosed by guide 100. In a further aspect of the present disclosure, the concave groove 102 is sized and shaped to allow for an endoscope to be inserted into the trachea alone or with the addition of an airway being inserted substantially along the valley of the parabolic surface.

In a particular embodiment, inside curved side 121 is characterized by forming a smooth parabolic curved trajectory between opposed sides 111(a) and 111(b). The curved surface of inside curved side 121 can be formed substantially similar to the parabolic cross section associated with concave groove 102. A curved inside curved side 121 allows for relatively simple fabrication through exemplary techniques such as extrusion and bending.

Smooth surface 101 defines a passageway (i.e. air space) for an exemplary medical device, such as endotracheal intubation device 10 from FIG. 1, to pass through into the trachea of the patient relatively easily. Medical professional M can leverage the inserted first leg 112 of guide 100 to elevate the tongue and surrounding soft tissue of patient P. Inside curved side 121 is typically in physical contact with at least the tongue and maybe the surrounding soft tissue of the patient during guide 100 use and insertion. This allows medical professional M to elevate the necessary tissues to allow for efficient and effective insertion of appropriate medical devices.

In an exemplary embodiment, guide 100 further comprises a maneuvering member 114 positioned at the opposed end 110 with respect to end 120. Maneuvering member 114 is adapted to allow for manual control over the position of first leg 112 relative to Patient P's anatomical structures such as the trachea for example. An exemplary guide 100 can comprise maneuvering member 114 that is a handle. The handle should be designed and configured to provide effective gripping for a medical professional and easy maneuverability of the opposed first leg 112.

The present disclosure provides for an exemplary guide 100 comprising an integral curved shaped member 111 that defines a U-shape geometry. Member 111 further comprises an opposed second leg 114 positioned opposite first leg 112. Second leg 114 can be integral with center portion 113 and first leg 112. As second leg 114 curves inward from center portion 113, the U-shape geometry is formed. The curving of second leg 114 defines a second angle A2 as seen with respect to FIG. 2. Typically at least end 120 is rounded. In a particular U-shaped embodiment, both ends 110 and 120 are rounded. Rounding the ends 110 and 120 enables insertion of guide 100 into the trachea.

In an exemplary integrally formed U-shaped embodiment of guide 100, angle A2 of second leg 114 should be configured and dimensioned to allow for second leg 114 to pass through the mouth and into the trachea of patient P. Generally, angle A1 can range from about 20 to 85 degrees and angle A2 can range from about 5 to 60 degrees. A particular aspect of the present disclosure describes an angle A1 to be about 80 degrees and angle A2 to be about 45 degrees. Typically the angles A1 and A2 relate from the tip of each end 110 and 120 and the center portion 113 defining the trajectory of the slope of each leg 112 and 114 respectively.

In an exemplary embodiment, the length of and integrally formed guide 100 from end 110 to end 120 ranges from about 7 to 12 inches of curved length. Each of the opposed sides 111(a) and 111(b) define a uniform outer thickness extending from each end of the guide. The thickness typically can range from about 0.5 to 2 inches. Concave groove 102 is cut out forming an air space sufficient to allow for efficient and effective insertion of a medical device. The airspace can be defined in patient P's throat after insertion of guide 100. The medical device can be any medical device desired to reach a target tissue region that maybe guided by guide 100.

Figure 4:
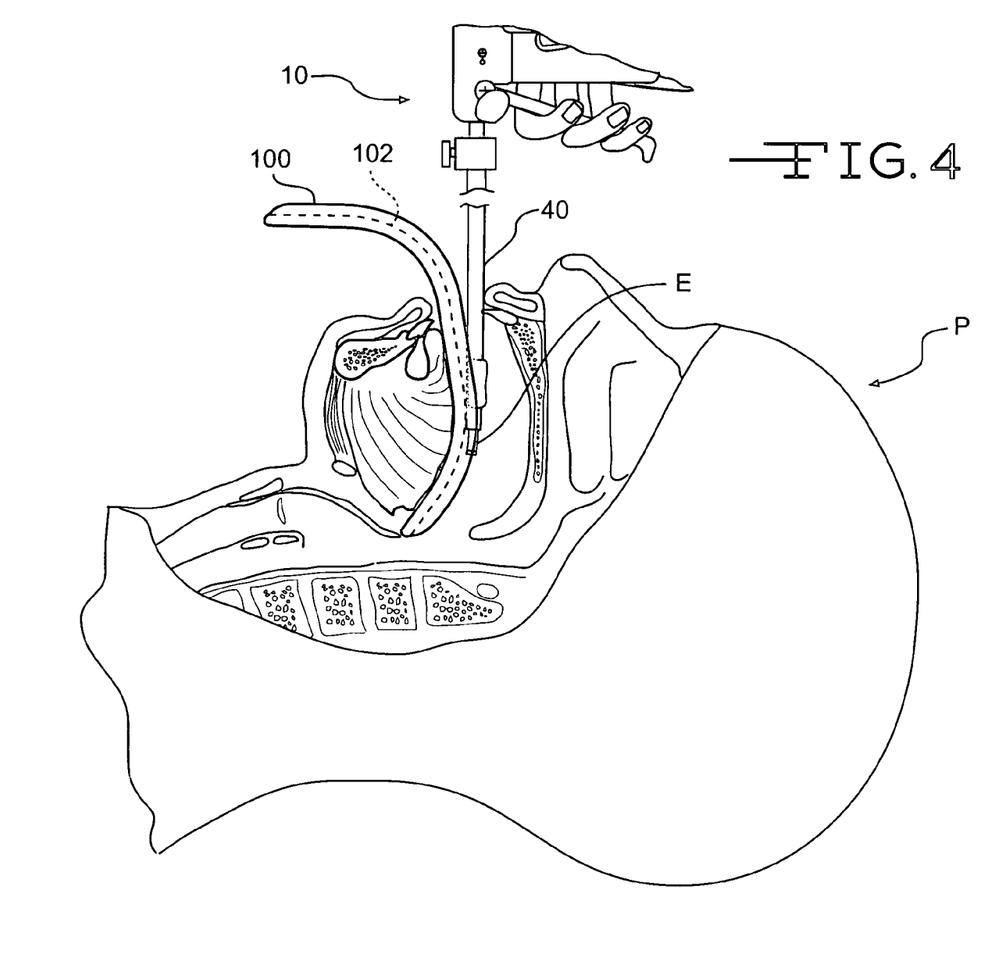
FIG. 4 illustrates a side view of an exemplary medical device being inserted along a passageway defined by an exemplary guide.
Figure 5:
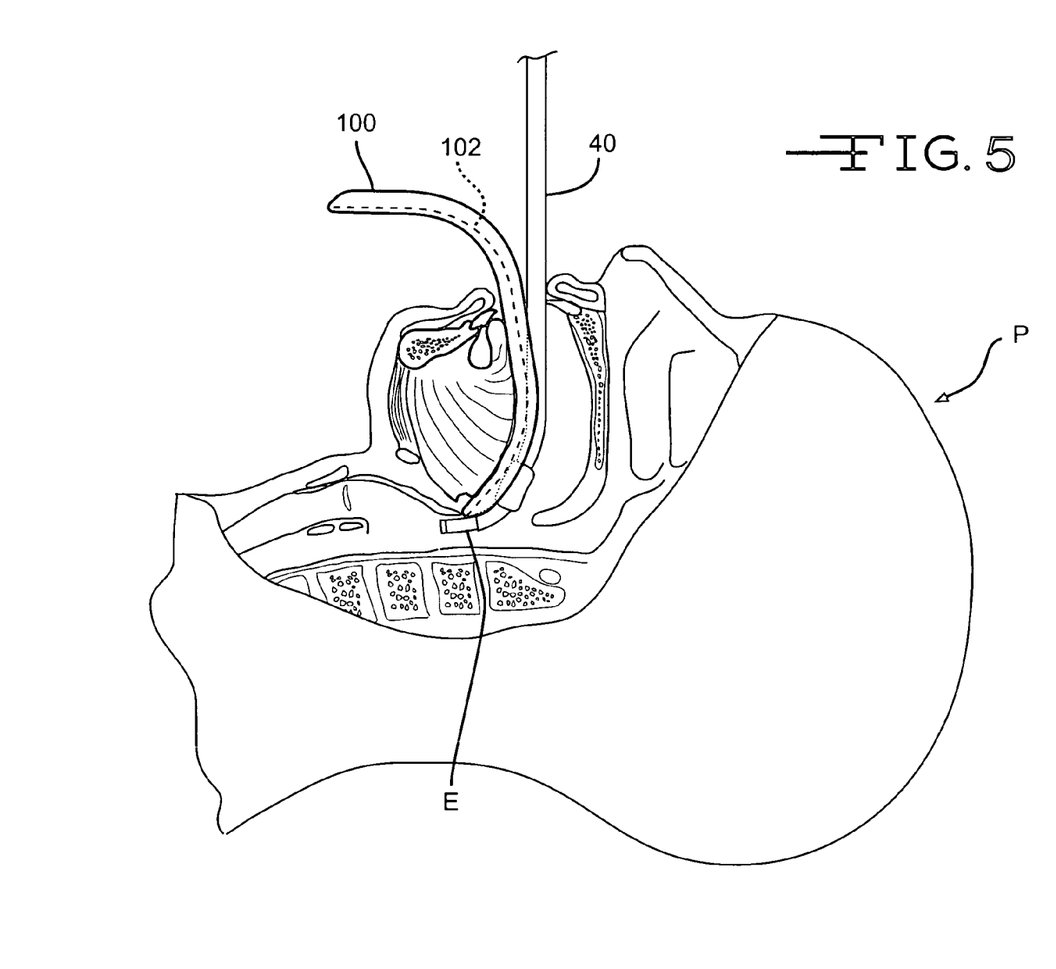
FIG. 5 illustrates the side view of FIG. 4 with the medical device inserted into the throat of the patient following along the curved portion associated with the exemplary guide.
Figure 6:
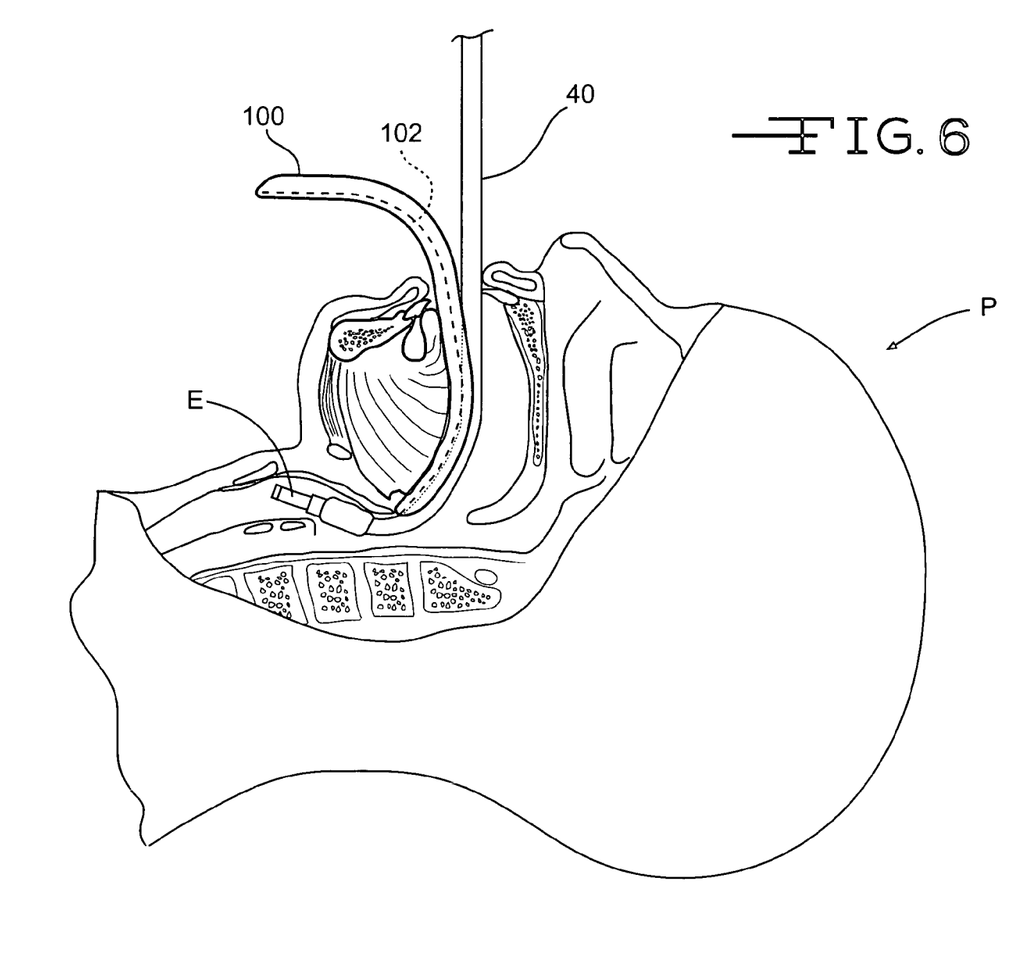
FIG. 6 illustrates the side view of FIG. 5 with the medical device fully inserted into the throat of the patient into the trachea following along the passageway defined by the guide.

In an exemplary embodiment, the medical device is an endoscope E or comprised within endotracheal intubation device 10 that is adapted to be received along surface 101 of concave groove 102. The medical device can further comprise an airway. In a particular embodiment as illustrated in FIGS. 4-6, endoscope E can be inserted along the passageway defined by guide 100.

Endoscope E can be formed to curve and follow the curvature defined by guide 100 through the mechanism described with respect to endotracheal intubation device 10 as described in Ser. No. 11/880,117. FIG. 4 illustrates the placement of guide 100 into the mouth and throat of Patient P. Device 10 aligns the tubular element 40 and endoscope E along concave groove 102 represented by a dotted line. FIG. 5 illustrates the curving of tubular element 40 and endoscope E effectuated by the mechanism of device 10. The curving follows the curving of guide 100. FIG. 6 illustrates the full insertion of endoscope E into the trachea of patient P. In an exemplary embodiment, endoscope E is used simultaneously with guide 100 to assist in positioning guide 100 since endoscope E is typically in cooperation with an imaging system. The imaging system allows for medical professional M to accurately and precisely position guide 100 in a desired location. Similarly, guide 100 along with an endoscope can work in cooperation to appropriately insert an airway into the trachea of patient P. Once the airway is positioned in a desired location, guide 100 and endoscope E can be removed.

In the medical field, when a patient requires intubation, time is of the essence. A medical professional's ability and efficiency in correctly intubating a patient can mean the difference between life and death. A guide as described with respect to exemplary embodiments in the present disclosure can define a smooth surface and be sized and dimensioned to effectively define an air space for speedy and effective on site intubation. Moreover, the guide can be configured to prevent injury to surrounding tissue regions such as the vocal cords during medical device insertion.

The guide can be fabricated from any plastic or composite material. Particularly, a material can be used that is cost effective, stable and safe. In an exemplary embodiment, guide 100 is fabricated from a member of the group consisting of polycarbonate, nylon and metal. The guide can be formed through extruding or injection molding. Typically the angles A1 and A2 can have an angle offset of about ±5% from a desired value.

Although the present disclosure is described herein with reference to illustrated embodiments, it should be understood that the invention is not limited hereto. Those having ordinary skill in the art and access to the teachings herein will recognize additional modifications and embodiments within the scope thereof. Accordingly, such modifications and/or embodiments are considered to be included within the scope of the present disclosure.

We claim:

1. A guide adapted to be inserted into the trachea of a patient to elevate the tongue and soft tissue of the patient to provide an air space for subsequent passage of a medical device, comprising:
   a member having a straight elongate center portion defining a longitudinal axis, and integral first and second elongate legs, each leg extending in a common plane at respective first and second angles from a respective end of the center portion; and
   the member having a uniform axial cross-sectional shape along the entire length of the center portion and the legs, the axial cross-sectional shape defining a parabolic geometry, which further defines a concave groove that extends along the entire length of the member to facilitate positioning of the medical device through the air space defined between the groove and the trachea of the patient; and wherein each of the first and second legs is configured and dimensioned to allow either of the legs to pass through a mouth and into a trachea of a patient.

2. The guide of claim 1, further comprising a first curved section connecting the first leg to the center portion and a second curved section connecting the center portion to the second leg.

3. The guide of claim 1, wherein the first angle is about 80° and the second angle is about 45°.

4. The guide of claim 1, wherein the air space defined by the concave groove allows insertion of the medical device such that the medical device avoids direct physical contact with the vocal cords.

5. The guide of claim 1, wherein the first leg of the guide is fabricated from a material selected from the group consisting of polycarbonate, nylon, and metal.

6. A method for facilitating insertion of a medical device into the trachea of a patient comprising the steps of:
 (a) inserting the guide of claim 1 into the trachea of the patient;
 (b) forming a passageway for the medical device to reach a target region by elevating the tongue and surrounding soft tissue of the patient with the inserted guide; and
 (c) inserting the medical device into the trachea to reach the target tissue region such that the medical device follows along a pathway defined by the concave groove formed on the outside curved side of the guide.

7. The method of claim 6, wherein the second angle ranges from about 20 to 60°.

8. The method of claim 6, wherein the first angle is about 80° and the second angle is about 45°.

9. The method of claim 6, wherein the medical device comprises an endoscope adapted to be received along a surface of the concave groove.

10. The method of claim 9, wherein the medical device further comprises an airway.

11. The method of claim 6, wherein the concave groove is configured and dimensioned to define the passageway that allows insertion of the medical device to reach the target region of the patient and passage by the vocal cords.

12. The method of claim 11, wherein the passageway defined by the concave groove allows insertion of the medical device such that the medical device avoids direct physical contact with the vocal cords.

13. The method of claim 6, wherein the first leg of the guide is fabricated from a material selected from the group consisting of polycarbonate, nylon, and metal.

14. The method of claim 6, wherein:
 (A) the medical device is an endoscope comprising a tubular element and a viewing means at a distal end of the tubular element and
 (B) the method further comprises the steps of:
  (i) inserting the tubular element of the endoscope into the trachea along the passageway formed by the guide;
  (ii) positioning the guide in a desired position and orientation using an image generated through the viewing means at the distal end of the tubular element of the endoscope; and
  (iii) inserting an airway to reach a target tissue region following along the guide to avoid causing harm to the surrounding soft tissue, the vocal cords, and the esophagus.

* * * * *